(12) United States Patent  
Lee et al.

(10) Patent No.: US 9,269,908 B2
(45) Date of Patent: Feb. 23, 2016

(54) BIPOLAR COMPOUND AS A HOST MATERIAL FOR ORGANIC LIGHT EMITTING DIODES

(75) Inventors: Chun Sing Lee, Hong Kong (HK); Xiao Hong Zhang, Hong Kong (HK); Shuit Tong Lee, Hong Kong (HK); Caijun Zheng, Hong Kong (HK); Man Keung Fung, Hong Kong (HK)

(73) Assignee: NANO AND ADVANCED MATERIALS INSTITUTE LIMITED, Hong Kong (HK)

( * ) Notice: Subject to any disclaimer, the term of this patent is extended or adjusted under 35 U.S.C. 154(b) by 969 days.

(21) Appl. No.: 13/450,493

(22) Filed: Apr. 19, 2012

(65) Prior Publication Data

US 2013/0099207 A1 Apr. 25, 2013

Related U.S. Application Data

(60) Provisional application No. 61/457,557, filed on Apr. 21, 2011.

(51) Int. Cl.
| | |
|---|---|
| *B32B 9/04* | (2006.01) |
| *C09K 11/00* | (2006.01) |
| *H01L 51/00* | (2006.01) |
| *H01L 51/56* | (2006.01) |
| *C07D 209/82* | (2006.01) |

(Continued)

(52) U.S. Cl.
CPC .......... *H01L 51/0072* (2013.01); *C07D 209/82* (2013.01); *C07D 471/04* (2013.01); *H01L 51/56* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 7,282,586 B1 | 10/2007 | Yen | |
| 2005/0037232 A1* | 2/2005 | Tyan et al. | 428/690 |

(Continued)

OTHER PUBLICATIONS

M.A. Baldo et al., "Highly efficient phosphorescent emission from organic electroluminescent devices" Letters to nature (395) p. 151-154, 1998.

(Continued)

*Primary Examiner* — J. L. Yang
(74) *Attorney, Agent, or Firm* — Ella Cheong Hong Kong; Sam T. Yip

(57) ABSTRACT

The present invention provides a bipolar compound represented by formula (I) and the derivatives thereof as a host material having excellent bipolar transporting properties for organic light-emitting diodes (OLEDs). The present invention also relates to a device including at least a layer of the bipolar compound and/or the derivatives thereof as a host material and a method of making the same.

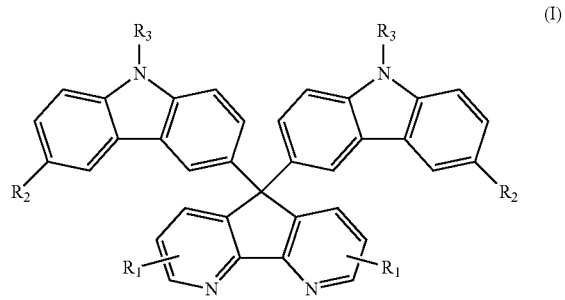

21 Claims, 14 Drawing Sheets

(51) Int. Cl.
*C07D 471/04* (2006.01)
*H01L 51/50* (2006.01)

(56) References Cited

U.S. PATENT DOCUMENTS

2008/0161574 A1 7/2008 Ohrui et al.
2008/0166591 A1 7/2008 Yamada et al.

OTHER PUBLICATIONS

Ken-Tsung Wong et al., "4,5-Diazafluorence-Incorporated Ter(9,9-diarylfluorene): A Novel Molecular Doping Strategy for Improving the Electron Injection Property of a Highly Efficient OLED Blue Emitter", Organic Letters (7), p. 1979-1982, 2005.

Brunner et al., "Carbazole Compounds as Host Materials for Triplet Emitters in Organic Light-Emitting Diodes: Tuning the HOMO Level without Influencing the Triplet Energy in Small Molecules", J. Am. Chem. Soc. 2004, 126, 6035-6042.

Wong et al., "4,5-Diazafluorene-Incorporated Ter(9,9-diarylfluorene): A Novel Molecular Doping Strategy for Improving the Electron Injection Property of a Highly Efficient OLED Blue Emitter", Org. Lett., vol. 7, No. 10, 2005, 1979-1982.

Baldo et al., "Highly efficient phosphorescent emission from organic electroluminescent devices", Nature, vol. 395, Sep. 10, 1998, 151-154.

* cited by examiner

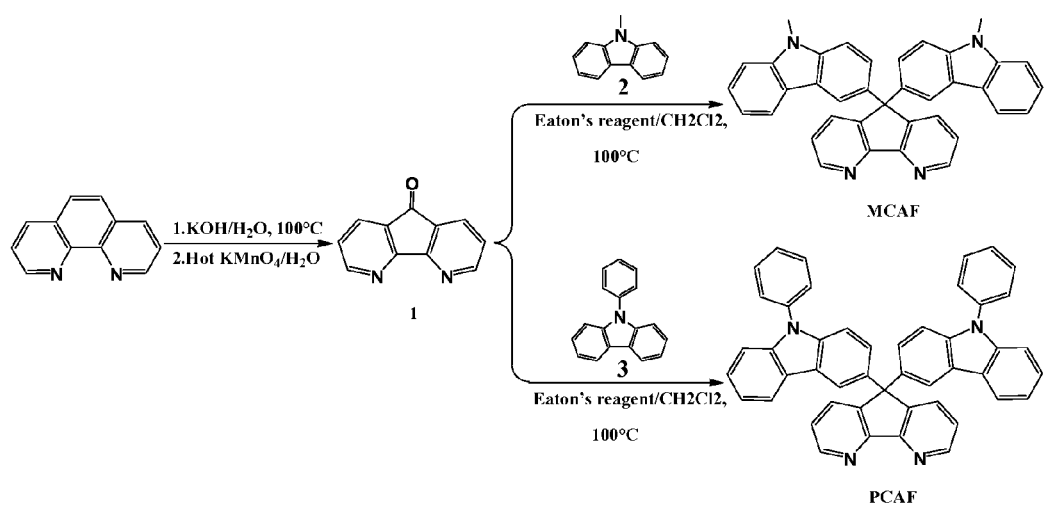
Figure 6. Syntheses of compound 11 (MCAF) and compound 12 (PCAF).

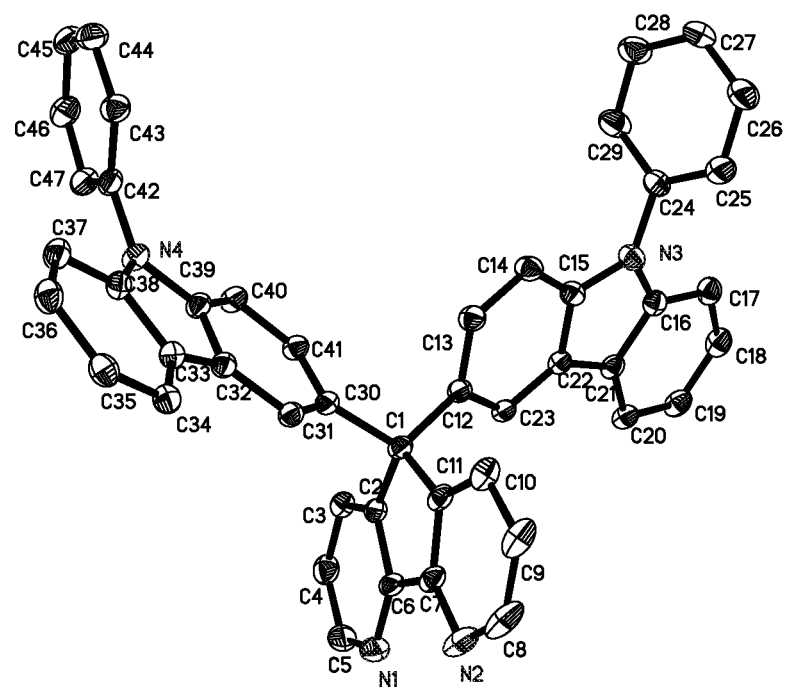
Figure 7. ORTEP diagram of compound 12.

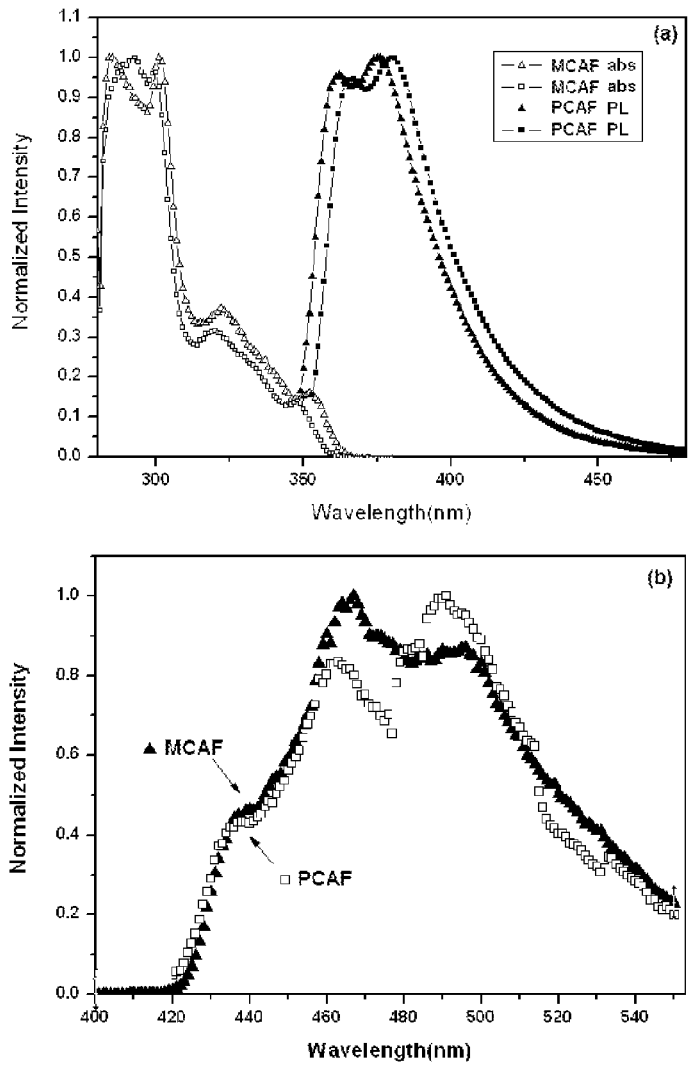
Figure 8. (a) Absorption and PL spectra of compound 11 (MCAF) and compound 12 (PCAF) in dilute toluene solution at room temperature. (b) The phosphorescence spectra of compound 11 (MCAF) and compound 12 (PCAF) in 2-MeTHF glass matrix at 77 K.

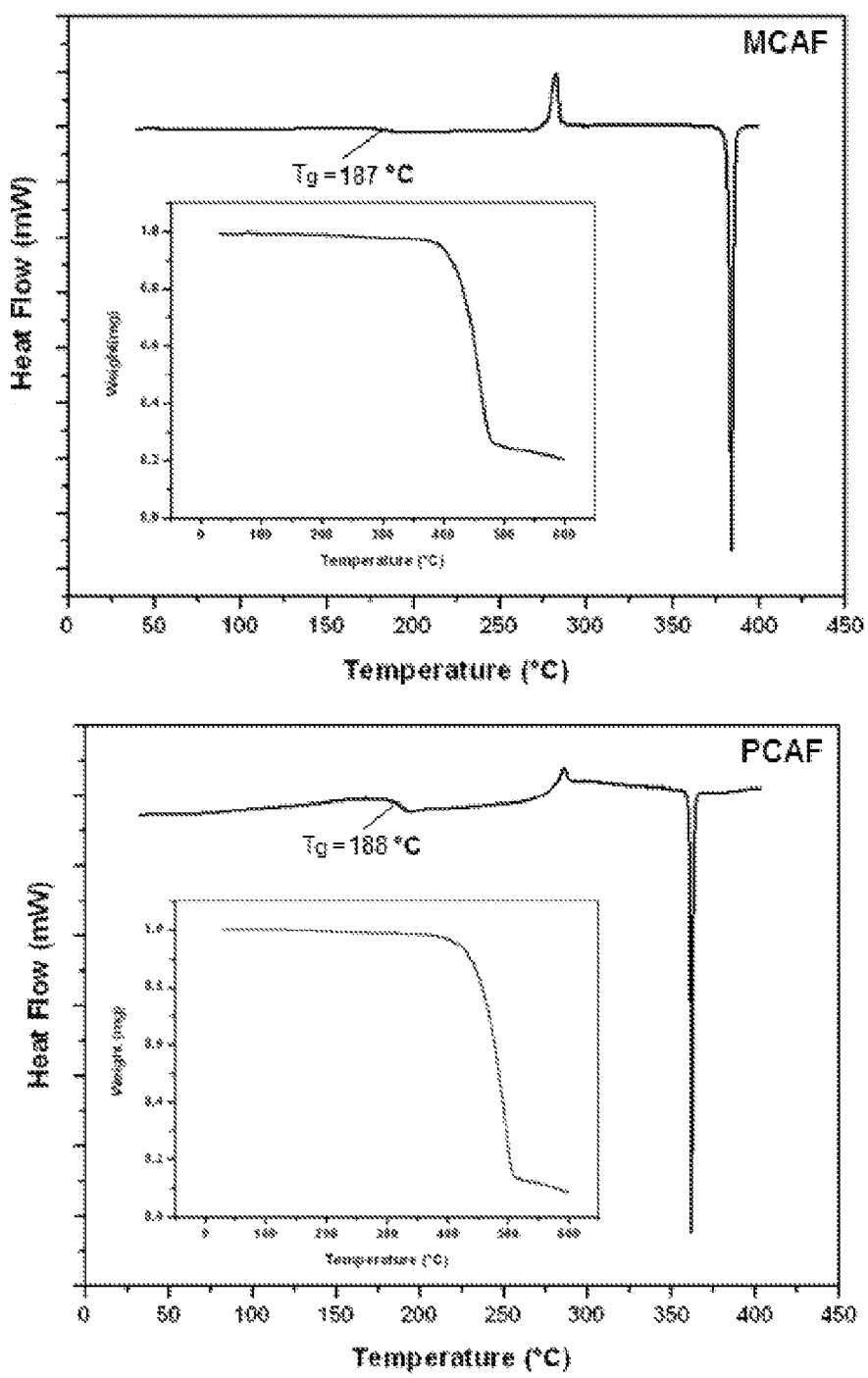
Figure 9. DSC and TGA (insert) curves of compound 11 (MCAF) and compound 12 (PCAF).

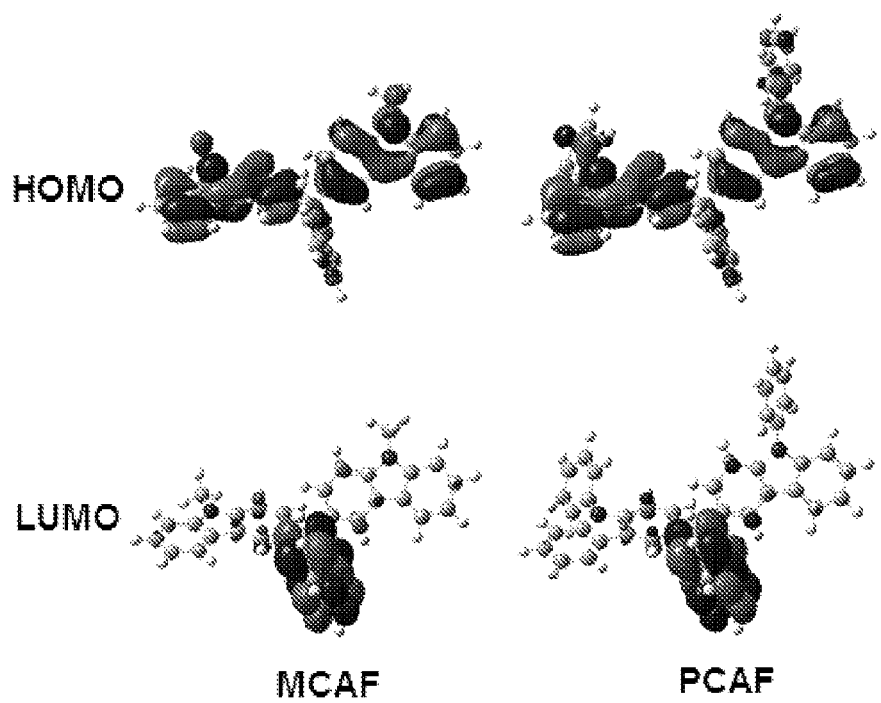
Figure 10. Calculated spatial distributions of the HOMO and LUMO energy densities of compound 11 (MCAF) and compound 12 (PCAF).

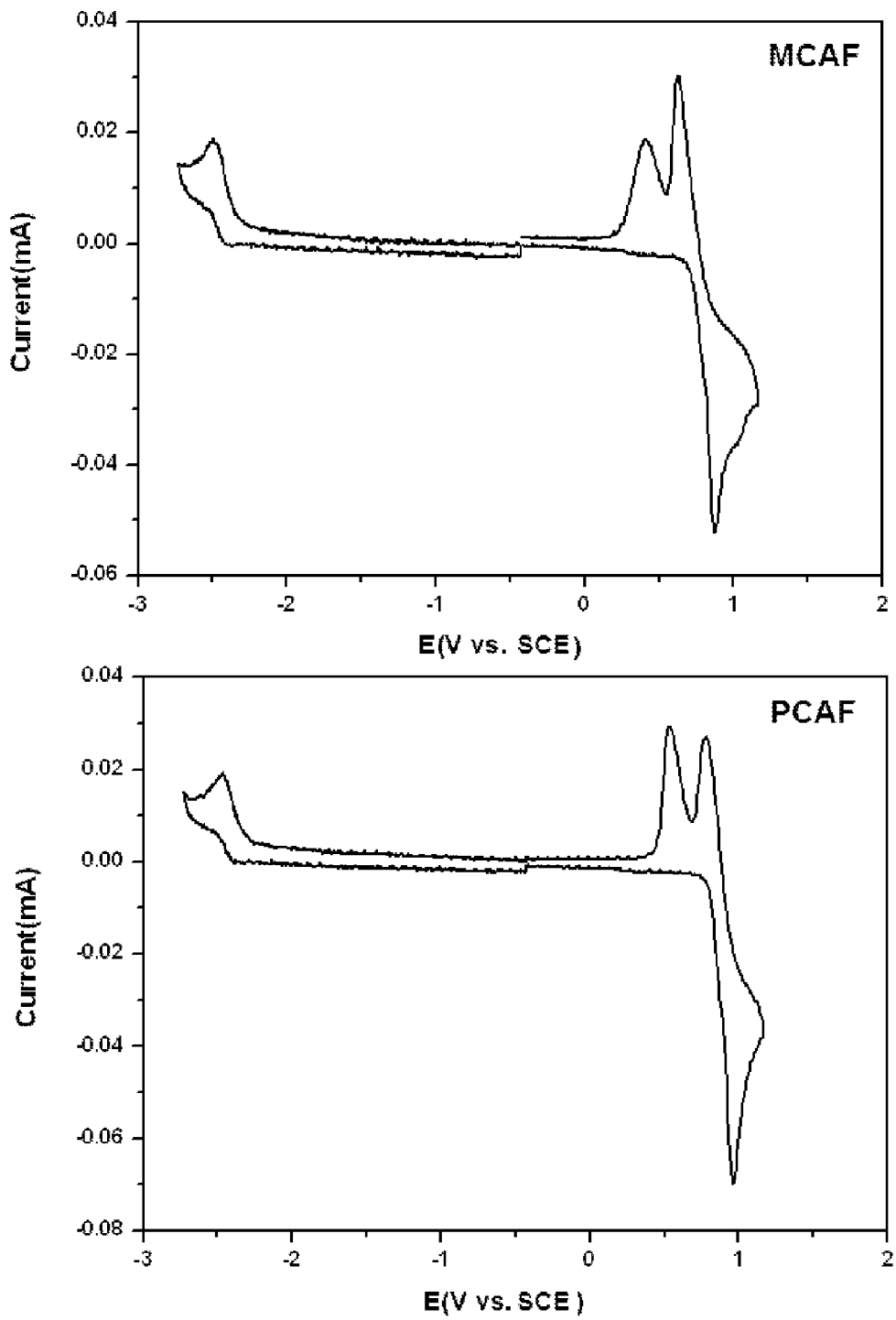
Figure 11. Cyclic voltammograms of compound 11 (MCAF) and compound 12 (PCAF).

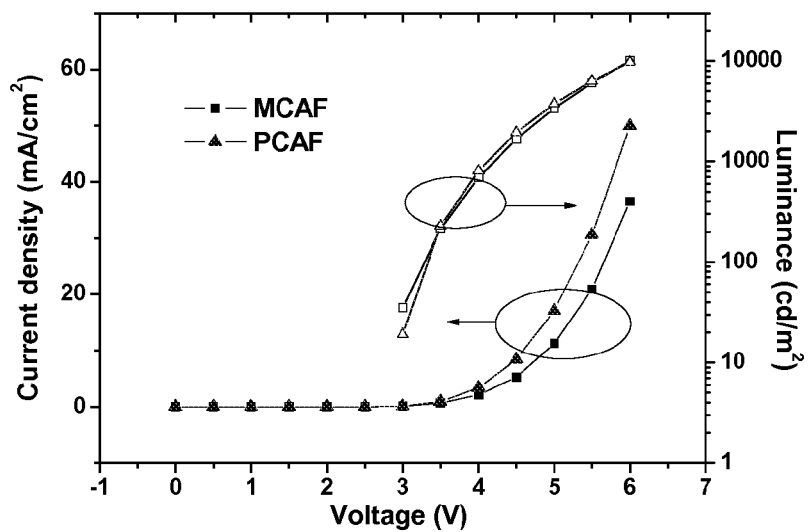
Figure 12. Current density-voltage and luminance-voltage characteristics of the PHOLEDs with compound 11 (MCAF) and compound 12 (PCAF).

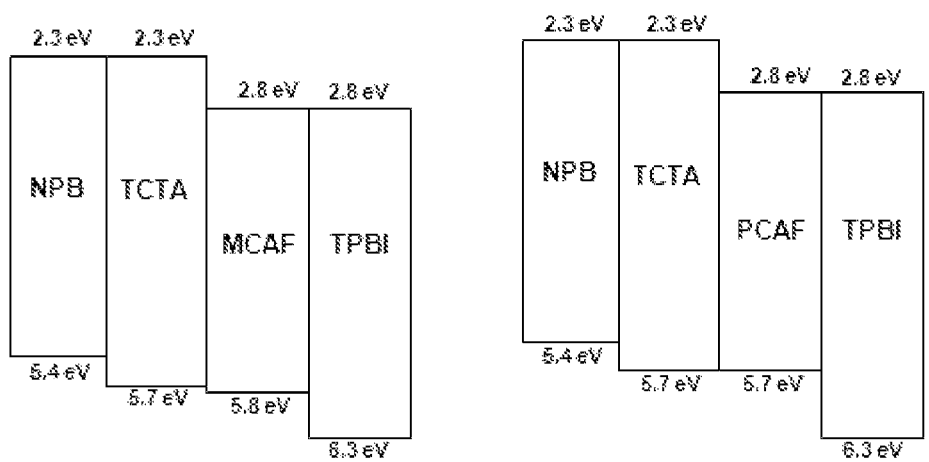
Figure 13. Relative energy level alignments of the PHOLEDs. Compound 11: MCAF; compound 12: PCAF.

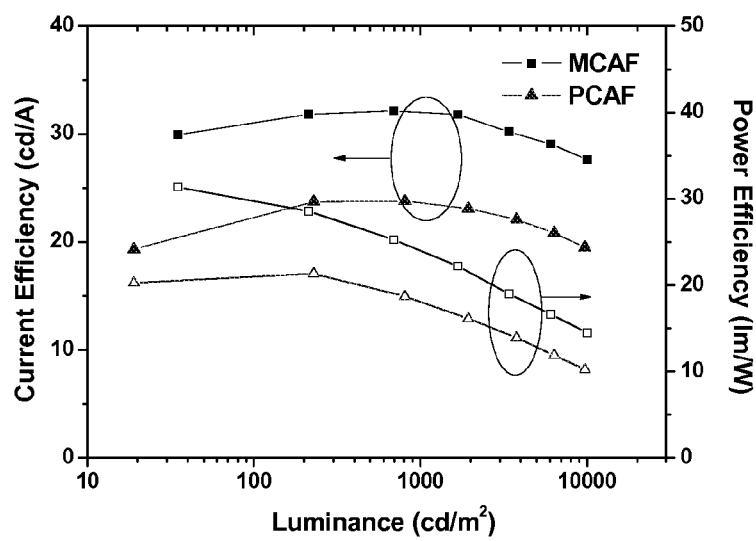
Figure 14. Current efficiency-luminance and power efficiency-luminance plots of the compound 11 (MCAF) and compound 12 (PCAF) based devices.

BIPOLAR COMPOUND AS A HOST MATERIAL FOR ORGANIC LIGHT EMITTING DIODES

CROSS-REFERENCE TO RELATED APPLICATIONS

The present application claims priority of U.S. provisional application Ser. No. 61/457,557 filed Apr. 21, 2011, and the disclosure of which is incorporated herein by reference and its entirety.

FIELD OF THE INVENTION

The present invention provides a bipolar compound and the derivatives thereof as a host material having excellent bipolar transporting properties for organic light-emitting diodes (OLEDs). The present invention also relates to a device including one or more layers of the bipolar compound and/or the derivatives thereof as a host material and a method of making the same.

TECHNICAL BACKGROUND

Since the first report of phosphorescent organic light-emitting devices (PHOLEDs) by Forrest et al. in 1998, PHOLEDs have attracted much attention because they can achieve an internal quantum efficiency of 100%. Phosphorescent emitters typically have long lifetimes and diffusion lengths; however, concentration quenching and T1-T1 annihilation are normally major causes for the poor device performance when the emitter concentration is high. To solve these problems, PHOLEDs are always fabricated by doping the phosphorescent emitters into a suitable host material so as to reduce the emitter concentration. Therefore, the development of host materials is of extremely crucial for efficient electrophosphorescence.

An efficient host material should have a desirable bandgap for effective energy transfer to the guest, good carrier transporting properties for a balanced recombination of carriers in the emitting layer, energy-level matching with neighboring layers for effective charge injection, and decent thermal and morphological stabilities for extending the device's lifetime. Traditional host materials usually only have single carrier transporting property, like N,N'-dicarbazolyl-3,5-benzene (mCP) and 3-(4-biphenylyl)-4-phenyl-5-(4-tert-butylphenyl)-1,2,4-triazole (TAZ). They only have hole-transporting and electron-transporting properties, respectively. This unbalanced carrier transporting property of host materials have been shown to be detrimental to the turn-on voltage and stability of OLEDs. Thereby, recently bipolar host materials which can balance the carrier transports have aroused extensive interests.

Because bipolar molecule must contain both the p- and n-type groups, intramolecular donor-acceptor interaction will generally lower the triplet energy of the material. Therefore, recently reported bipolar hosts, like o-CzOXD and BUPH1, are mainly used in the green and red PHOLEDs. In contrast, bipolar hosts used in blue PHOLEDs are rarely reported. There are two possible regimes to obtain a bipolar blue host: either chemical groups which have extremely high triplet energies or a compound which the p-type group and n-type group are designed to be farther enough to decrease the intramolecular donor-acceptor interaction. However, the chemical groups with high triplet energies generally have small steric volumes. The bipolar compound might not have decent thermal and morphological stabilities.

SUMMARY OF THE INVENTION

In the present invention, the first aspect relates to a compound including two p-type carbazole groups and an n-type 4,5-diazafluorene group as the electron-donor units and an electron-acceptor unit respectively which is provided in formula (I):

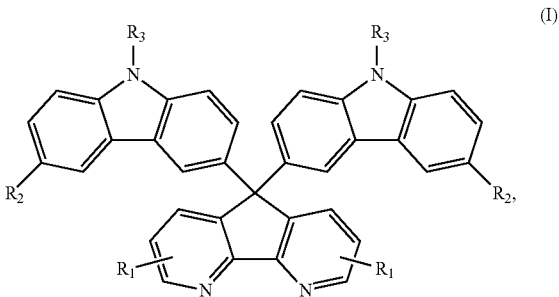

wherein $R_1$, $R_2$ and $R_3$ are independently or jointly selected from a hydrogen atom, a substituted or unsubstituted alkyl group, a substituted or unsubstituted aryl group, or a triarylsilyl group. The compound of formula (I) has a triplet energy level of at least 2.82 eV, a glass transition temperature of at least 187° C., and non-planar structures with substantially no intramolecular interaction between the carbazole groups and the 4,5-diazafluorene group.

The substituted or unsubstituted $C_{1-10}$ alkyl group for substituting the $R_1$, $R_2$ and/or $R_3$ of the compound of formula (I) is selected from one or more of a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, a 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, and an adamantyl group. Substituent(s) for the substituted groups of the substituted alkyl group is/are selected from one or more of alkyl groups, aryl groups, heterocyclic groups, substituted amino groups, alkoxy groups, halogen atoms, hydroxyl groups, cyano groups, or nitro groups.

The substituted or unsubstituted $C_{6-12}$ aryl group for substituting the $R_1$, $R_2$ and/or $R_3$ of the compound of formula (I) is selected from one or more of a phenyl group, a 4-methylphenyl group, a 4-methoxyphenyl group, a 4-ethylphenyl group, a 4-fluorophenyl group, a 4-trifluorophenyl group, a 3,5-dimethylphenyl group, a 2,6-diethylphenyl group, a mesityl group, a 4-tert-butylphenyl group, a ditolylaminophenyl group, and a biphenyl group. Substituent(s) for the substituted groups of the substituted aryl group is/are selected from one or more of alkyl groups, aryl groups, heterocyclic groups, substituted amino groups, alkoxy groups, halogen atoms, hydroxyl groups, cyano groups, or nitro groups.

The $C_{4-10}$ triarylsilyl group for substituting the $R_1$, $R_2$ and/or $R_3$ of the compound of formula (I) is selected from one or more of phenyl, 2-pyridyl, 3-pyridyl, 4-pyridyl, 2-thienyl, 1-naphthyl, 2-naphthyl, and quinine-2-yl. Substituent(s) for the substituted groups of the triarylsilyl group is/are selected from one or more of alkyl groups, aryl groups, heterocyclic groups, substituted amino groups, alkoxy groups, halogen atoms, hydroxyl groups, cyano groups, and nitro groups.

The second aspect of the present invention relates to a device including the compound of formula (I) and/or its derivatives for organic light-emitting diodes. The device of the present invention includes one or more layers of the compound of formula (I), at least one anode and one cathode, where the one or more layers of the compound of formula (I) is sandwiched between a pair of the anode and cathode. The device of the present invention may additionally include one or more of the following layers: a hole-injection layer, a hole-transporting layer, an electron-blocking layer, an emissive layer, a hole-blocking layer, a electron transporting layer, and/or a cathode buffer layer, and any of these additional layer(s) is/are sandwiched between a pair of the anode and cathode. The device itself can be an organic light-emitting diode or be part of an organic light-emitting diode.

The third aspect of the present invention also relates to a method of preparing the compound of formula (I) and/or the derivatives thereof. The method of preparing the compound of formula (I) and/or the derivatives thereof includes synthesizing a 4,5-diazafluoren-containing compound and/or its derivatives, synthesizing a carbazole-containing compound and/or its derivatives, reacting the 4,5-diazafluoren-containing compound and/or its derivatives with the carbazole-containing compound and/or its derivatives to form the compound of formula (I). The compound prepared by the method of the present invention can be used as a host material for organic light-emitting diode. The host material based on the compound of formula (I) can be fabricated into a layer and that layer can be sandwiched between a pair of anode and cathode or between a different combination of additional layers which are sandwiched between a pair of anode and cathode in order to form an organic light-emitting diode or a device for an organic light-emitting diode.

BRIEF DESCRIPTION OF THE DRAWINGS

FIG. 6: Schematic diagram depicting a synthesis scheme of compound 11 (MCAF) and compound 12 (PCAF).

FIG. 7: ORTEP diagram of compound 12.

FIG. 8: Absorption and PL spectra of compound 11 (MCAF) and compound 12 (PCAF) in dilute toluene solution at room temperature (8A); The phosphorescence spectra of compound 11 (MCAF) and compound 12 (PCAF) in 2-MeTHF glass matrix at 77 K (8B).

FIG. 9: DSC and TGA (insert) curves of compound 11 (MCAF) and 12 (PCAF).

FIG. 10: Calculated spatial distributions of the HOMO and LUMO energy densities of compound 11 (MCAF) and compound 12 (PCAF).

FIG. 11: Cyclic voltammograms of compound 11 (MCAF) and compound 12 (PCAF).

FIG. 12: Current density-voltage and luminance-voltage characteristics of the PHOLEDs with compound 11 (MCAF) and compound 12 (PCAF).

FIG. 13: Relative energy level alignments of the PHOLEDs. Compound 11: MCAF; Compound 12: PCAF.

FIG. 14: Current efficiency-luminance and power efficiency-luminance plots of the compound 11 (MCAF) and compound 12 (PCAF) based devices.

DETAILED DESCRIPTION OF THE INVENTION

Figure 1:
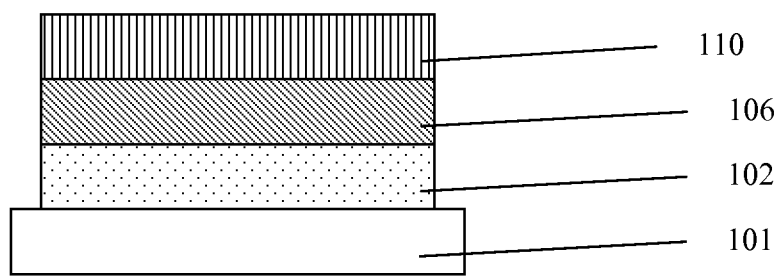
FIG. 1: A schematic diagram showing the first embodiment of the organic light-emitting device in accordance with the present invention.

The compound of the present invention as a bipolar host material for organic light-emitting diodes includes two carbazole units as electron donor and a 4,5-diazafluorene unit as electron acceptor such that the compound has non-planar structures with substantially no intramolecular interaction between the electron donor and acceptor. The compound has the following general formula (I):

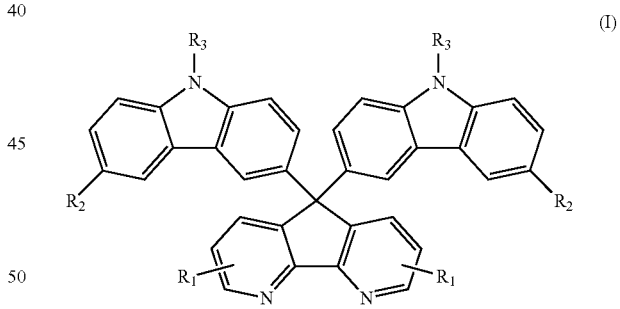

In formula (I), $R_1$, $R_2$, and $R_3$ are independently or jointly substituted by the following groups of compounds: a hydrogen atom, a substituted or unsubstituted alkyl group, a substituted or unsubstituted aryl group, or a triarylsilyl group.

Examples of the substituted or unsubstituted $C_{1-10}$ alkyl group for substituting $R_1$, $R_2$ and/or $R_3$ include a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, a 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, and an adamantyl group.

Examples of the substituted or unsubstituted $C_{6-12}$ aryl group for substituting $R_1$, $R_2$ and $R_3$ include a phenyl group, a 4-methylphenyl group, a 4-methoxyphenyl group, a 4-ethylphenyl group, a 4-fluorophenyl group, a 4-trifluorophenyl group, a 3,5-dimethylphenyl group, a 2,6-diethylphenyl group, a mesityl group, a 4-tert-butylphenyl group, a ditolylaminophenyl group, and a biphenyl group.

Examples of the $C_{4-10}$ triarylsilyl group for substituting $R_1$, $R_2$ and $R_3$ include phenyl, 2-pyridyl, 3-pyridyl, 4-pyridyl, 2-thienyl, 1-naphthyl, 2-naphthyl, and quinine-2-yl.

Examples of substituents for substitution in the substituted alkyl group or the substituted aryl group include: one or more $C_{1-3}$ alkyl groups such as a methyl group, an ethyl group, a propyl group, and a trifluoromethyl group; one or more $C_{6-12}$ aryl groups such as a phenyl group and a biphenyl group; one or more $C_4$ heterocyclic groups such as a thienyl group and a pyrrolyl group; one or more substituted amino groups such as a dimethylamino group, a diethylamino group, a dibenzylamino group, a diphenylamino group, a ditolylamino group, and a dianisolylamino group; one or more alkoxy groups such as a methoxy group and an ethoxy group; one or more halogen atoms such as fluorine, chlorine, bromine, and iodine; one or more hydroxyl groups; one or more cyano groups; and one or more nitro groups.

Examples of substituents for substitution in the triarylsilyl groups include: one or more $C_{1-3}$ alkyl groups such as a methyl group, an ethyl group, a propyl group, and a trifluoromethyl group; one or more $C_{6-12}$ aryl groups such as a phenyl group and a biphenyl group; one or more $C_4$ heterocyclic groups such as a thienyl group and a pyrrolyl group; one or more substituted amino groups such as a dimethylamino group, a diethylamino group, a dibenzylamino group, a diphenylamino group, a ditolylamino group, and a dianisolylamino group; one or more alkoxy groups such as a methoxy group and an ethoxy group; one or more halogen atoms such as fluorine, chlorine, bromine, and iodine; one or more hydroxyl groups; one or more cyano groups; and one or more nitro groups.

$R_1$, $R_2$ and $R_3$ may be the same or different from each other.

Some examples of the derivatives of the compound of formula (I), namely compounds 11-34, which are substituted at $R_1$, $R_2$ and $R_3$ by different chemical groups are shown below. However, these derivatives are only representative examples, and the present invention is not limited thereto.

11

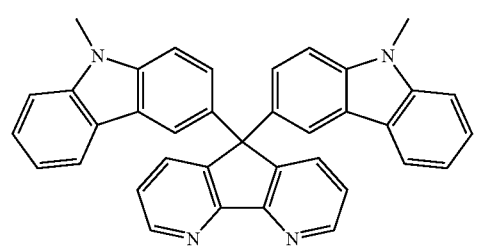

12

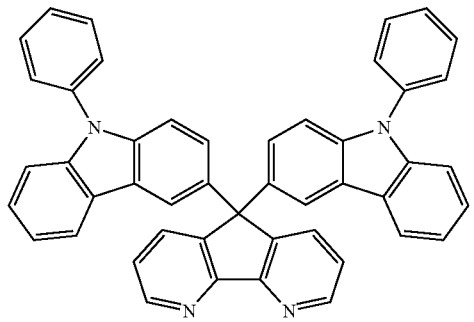

13

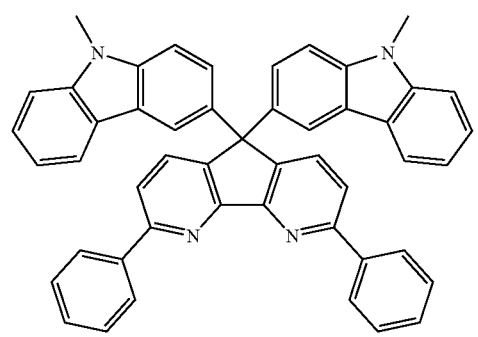

14

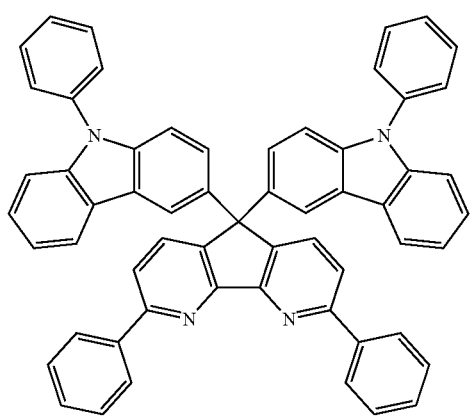

-continued
15
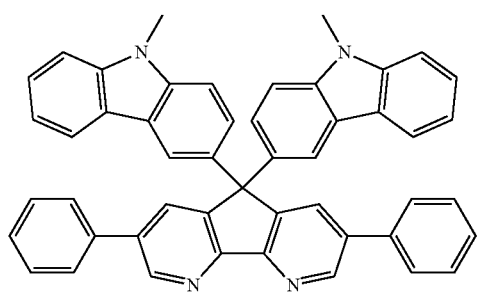
16
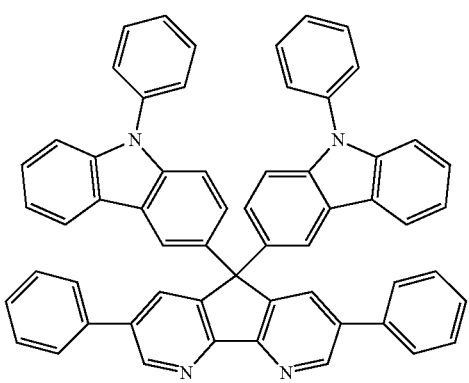
17
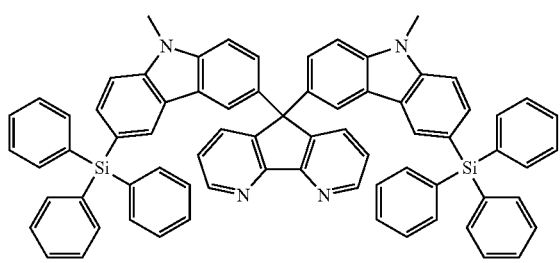
18
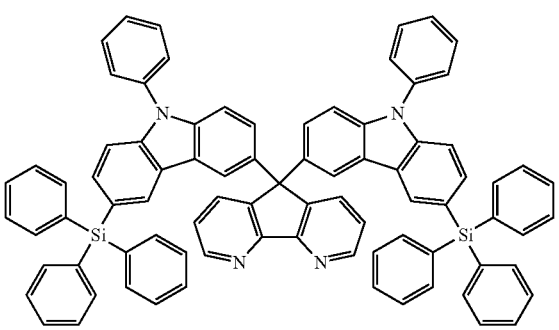
19
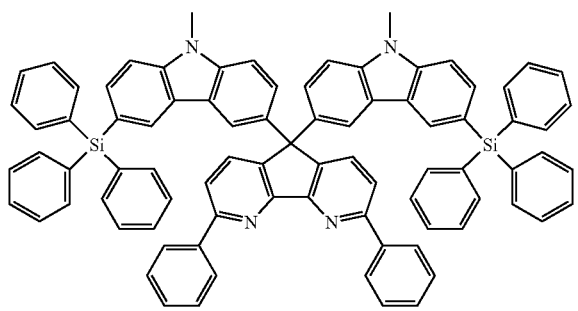
20
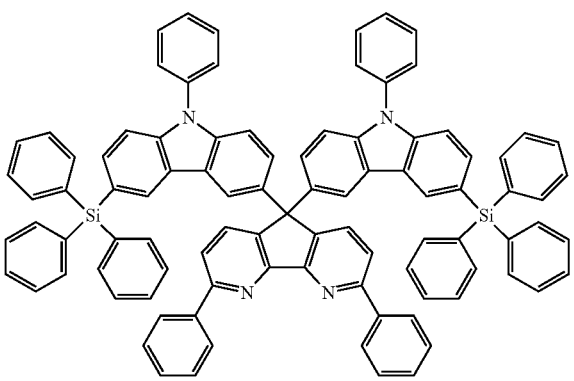
21
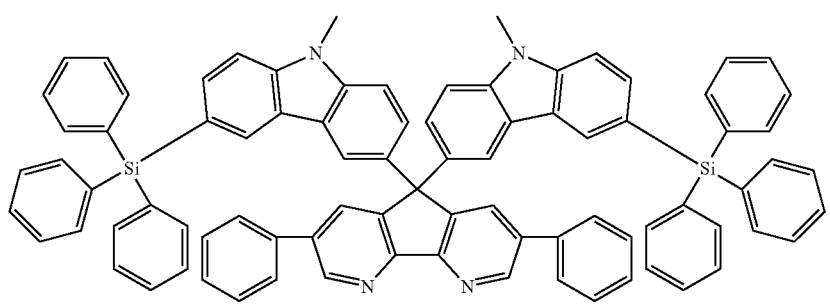

-continued
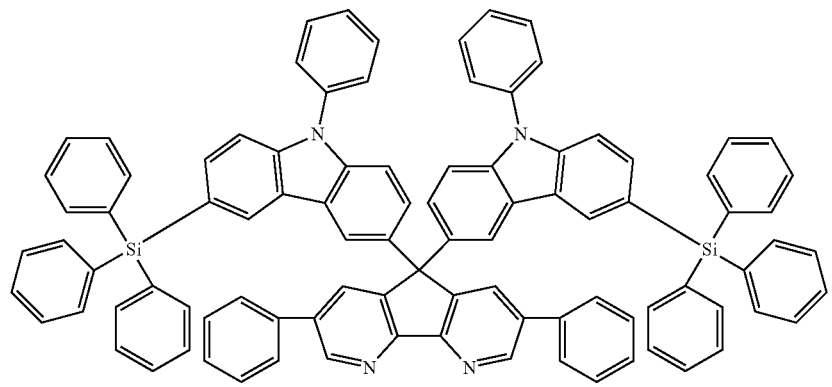
22
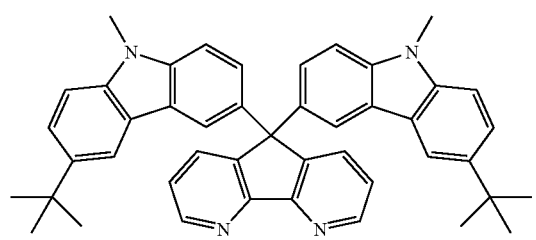
23
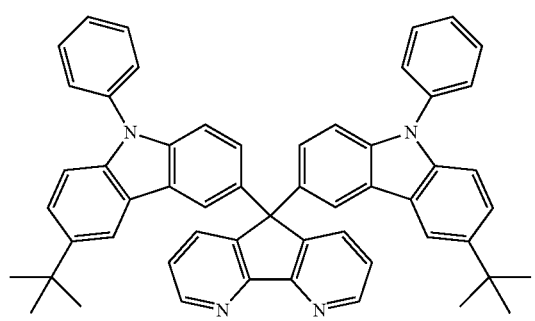
24
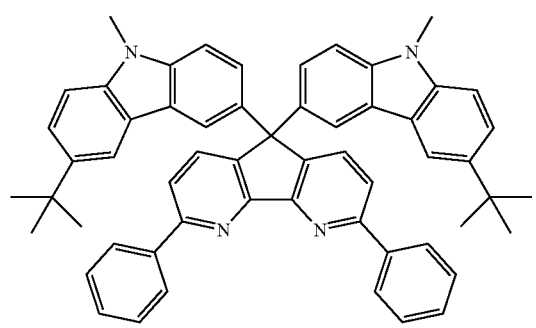
25
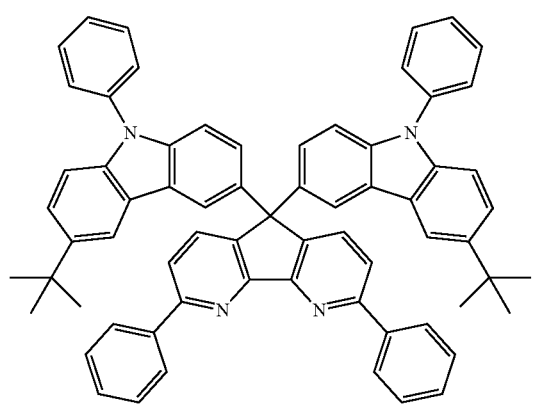
26
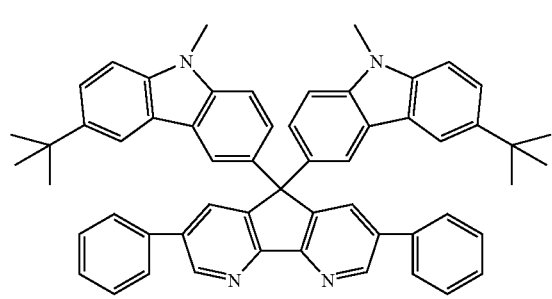
27
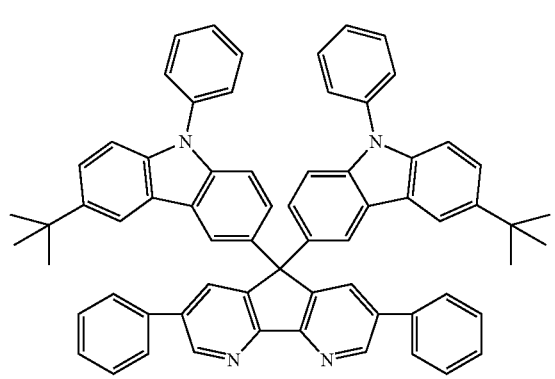
28

-continued

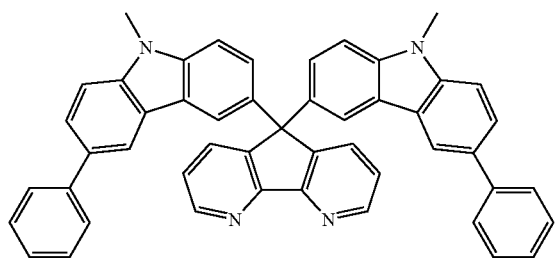
29

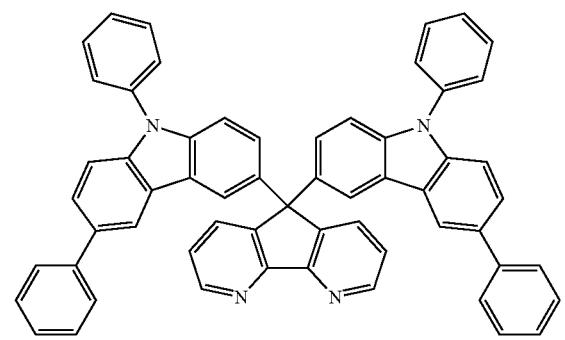
30

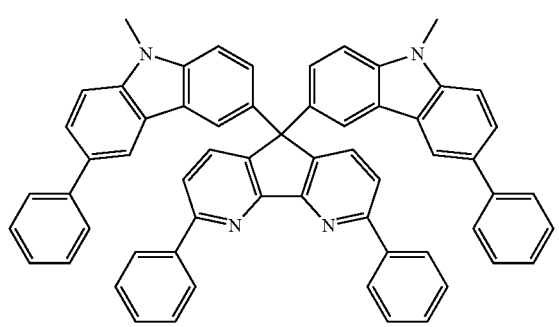
31

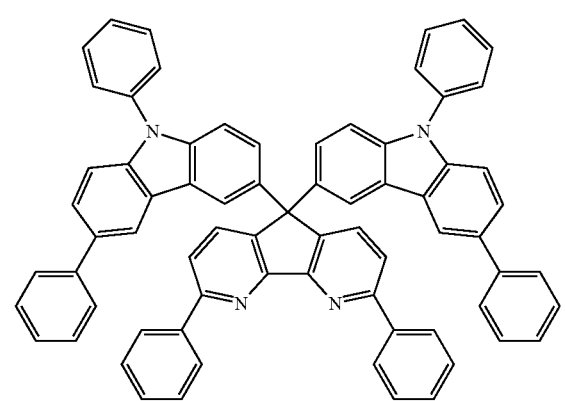
32

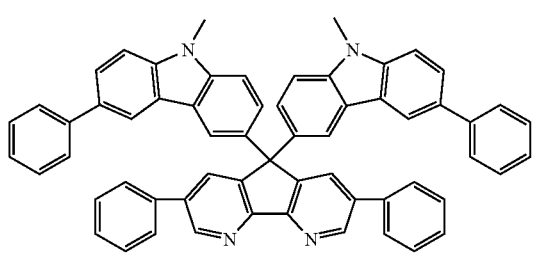
33

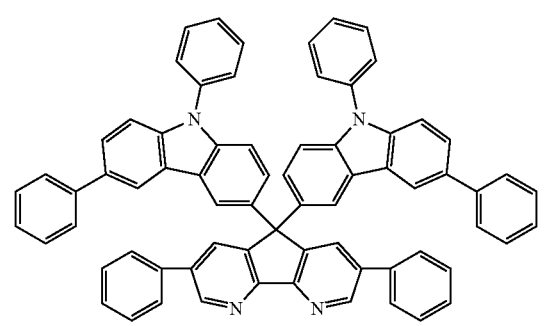
34

The compound of formula (I) of the present invention has a bipolar transporting property, high triplet energy of at least 2.82 eV, and a high glass transition temperature of at least 187° C. The compound of formula (I) can be used as a host material for organic light-emitting diodes and enhance the efficiency of the organic light-emitting diode when the compound is incorporated into the organic light-emitting diodes.

In an exemplary embodiment, compounds 11 and 12, namely 9,9-bis(9-methylcarbazol-3-yl)-4,5-diazafluorene (MCAF) and 9,9-bis(9-phenylcarbazaol-3-yl)-4,5-diazafluorene (PCAF), are preferred as the compound of the present invention for use in an organic light-emitting diode.

A device of the present invention includes a layer made of the compound of formula (I) and/or its derivatives, and the layer having the compound of formula (I) and/or its derivatives is sandwiched between at least a pair of electrodes including an anode and a cathode. The device of the present invention can be an organic light-emitting diode or be part of an organic light-emitting.

Further, the device of the present invention can be incorporated with additional layers. The additional layers which can be incorporated into the device of the present invention include hole-injection layer, hole-transporting layer, electron-blocking layer, emissive layer, hole-blocking layer, electron-transporting layer, cathode buffer layer. Examples of the device of the present invention incorporating different combination of layers are shown in FIGS. 1-6

In FIG. 1, 101 is a substrate of an organic light-emitting diode; 102 is an anode; 106 is an emissive layer; and 110 is a cathode. Examples of substrate which can be used are known to those skilled in the art, includes but not limited to glass, metal, semiconductor, insulator and polymer. The compound of formula (I) of the present invention is used as a host material and being incorporated with a guest molecule to form the emissive layer 106. A suitable guest molecule can be any kind of dopant known to those skilled in the art. A rare-earth metal complexes, such as iridium complexes, like FIrpic (iridium (III) bis[2-(4',6'-difluorophenyl)pyridinato-N,C (2')]-picolinate) may be used. The following sequence of layers in this example is from the bottom to the top: the substrate 101, the anode 102, the emissive layer 106, and the cathode 110.

Figure 2:
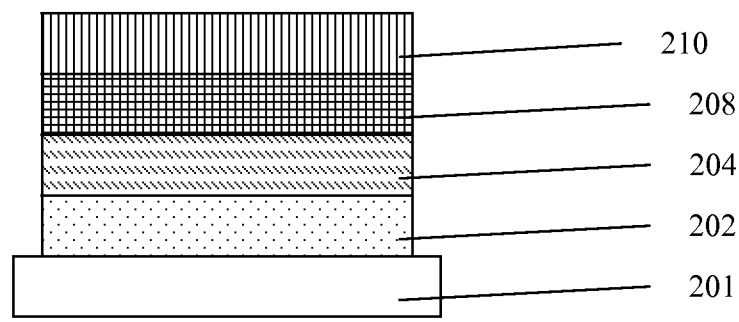
FIG. 2: A schematic diagram showing the second embodiment of the organic light-emitting device in accordance with the present invention.

In FIG. 2, 201 is a substrate of an organic light-emitting diode; 202 is an anode; 204 is a hole-transporting layer; 208 is an electron-transporting; and 210 is a cathode. The electron-transporting layer 208 or the hole-transporting layer 204 can also serve the same function of the emissive layer 106 as shown in FIG. 1. In this example, the compound of formula (I) of the present invention can be incorporated into either the electron-transporting layer 208, the hole-transporting layer 204 or both of them, where these layers contain a guest molecule. The following sequence of layers in this example is from the bottom to the top: the substrate 201, the anode 202, the hole-transporting layer 204, the electron-transporting layer 208, and the cathode 210. The sequence of the layers may be reversed so long as the function as an emission layer is maintained. For example, the sequence of layers can also be from the bottom to the top: the substrate 201, the cathode 210, the electron-transporting layer 208, the hole-transporting layer 204 and the anode 202.

Figure 3:
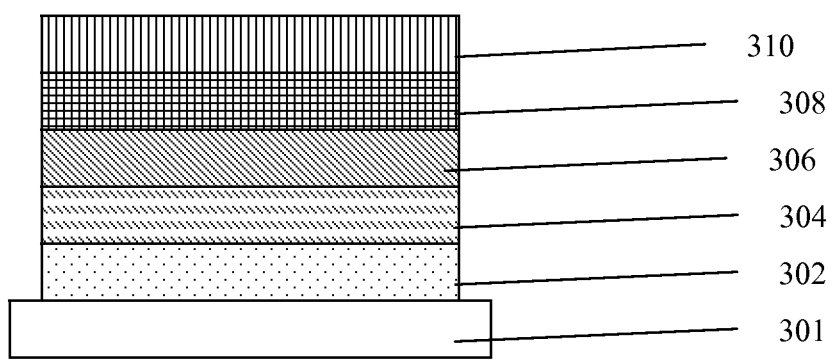
FIG. 3: A schematic diagram showing the third embodiment of the organic light-emitting device in accordance with the present invention.

In FIG. 3, 301 is a substrate of an organic light-emitting diode; 302 is an anode; 304 is a hole-transporting layer; 306 is an emissive layer; 308 is an electron-transporting layer; 310 is a cathode. The compound of formula (I) of the present invention can be incorporated into either the hole-transporting layer 304, the emissive layer 306, or both of them, where these layers contain a guest molecule. The following sequence of layers in this example is from the bottom to the top: the substrate 301; the anode 302; the hole-transporting layer 304; the emissive layer 306; the electron-transporting layer 308; the cathode 310.

Figure 4:
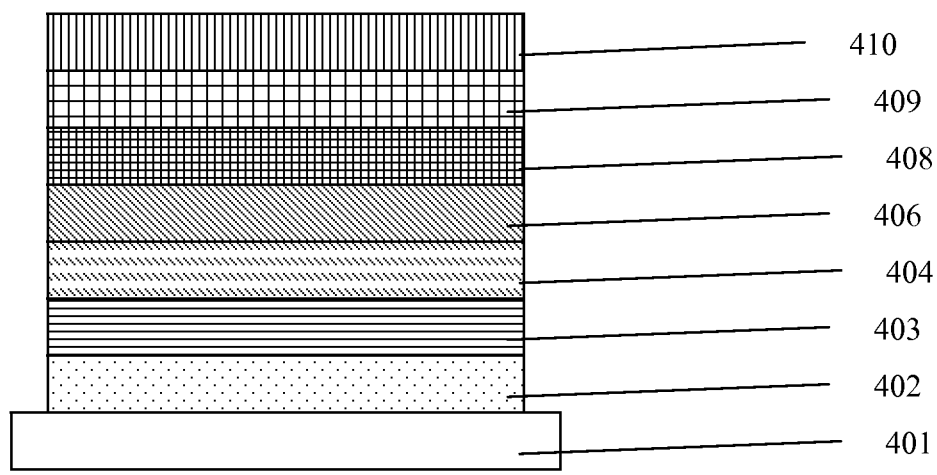
FIG. 4: A schematic diagram showing the fourth embodiment of the organic light-emitting device in accordance with the present invention.

In FIG. 4, 401 is a substrate of an organic light-emitting diode; 402 is an anode; 403 is a hole-injection layer; 404 is a hole-transporting layer; 406 is an emissive layer; 408 is an electron-transporting layer; 409 is a cathode buffer layer; and 410 is a cathode.

Figure 5:
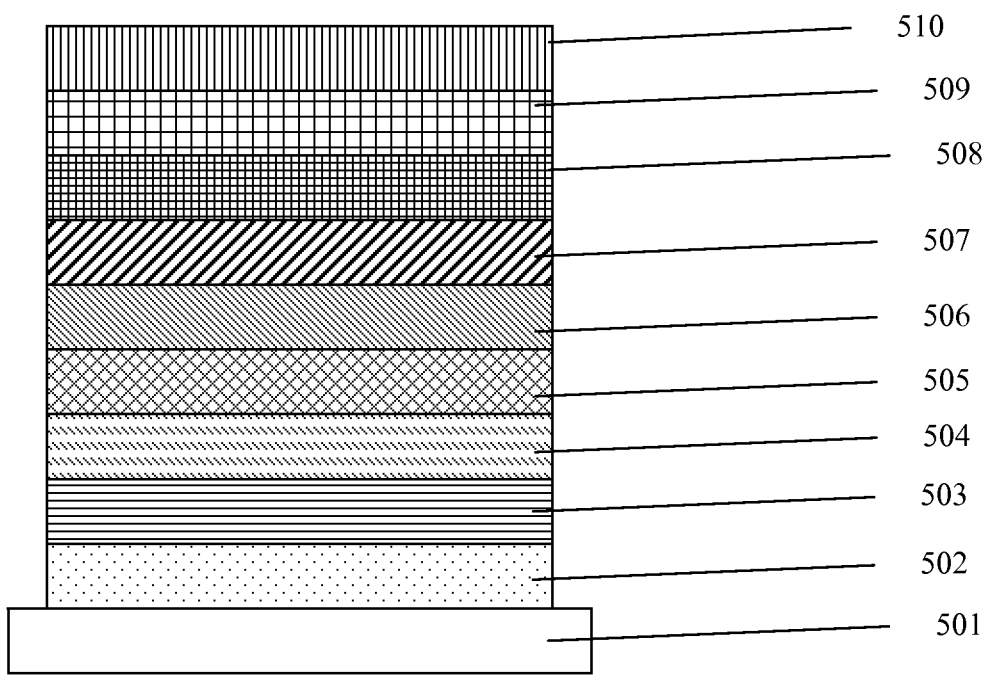
FIG. 5: A schematic diagram showing the fifth embodiment of the organic light-emitting device in accordance with the present invention.

In FIG. 5, 501 is a substrate of an organic light-emitting diode; 502 is an anode 2; 503 is a hole-injection layer; 504 is a hole-transporting layer; 505 is an electron-blocking layer; 506 is an emissive layer; 507 is a hole-blocking layer; 508 is an electron-transporting layer; 509 is a cathode buffer layer; and 510 is a cathode.

When the compound of formula (I) of the present invention is used as a host material in the device of the present invention, the compound of formula (I) and/or its derivatives is preferably used in combination with a guest molecule being incorporated into an emissive layer.

EXAMPLES

Example 1

Synthesis of Intermediate Compounds 1-3 (as Illustrated in FIG. 6)

4,5-Diazafluoren-9-one (named as compound 1 in FIG. 6)

To a boiling solution of phenanthroline monohydrate (2.2 g, 11.1 mol) and KOH (2 g, 35.5 mol) in water (130 ml), a hot solution of KMnO4 (5 g, 31.5 mol) in water (80 ml) was added dropwise over ca. 1 h. The mixture was refluxed for another 2 h, and then filtered hot. The orange filtrate was cooled and extracted with chloroform, the combined organic extracts were dried over anhydrous $Na_2SO_4$. After solvent removal, the crude product was further purified by column chromatography on silica gel using acetone/petroleum ether (2:1) as the eluent, the product was isolated as a yellow solid (980 mg, 48%). $^1$HNMR (ACETONE-D6, 400 MHz): δ=8.80 (d, J=5.0 Hz, 2H), 8.06 (d, J=7.5 Hz, 2H), 7.50 (dd, $J_1$=7.5 Hz, $J_2$=5.0 Hz, 2H). HRMS calcd for 182.1782, found 182.0369.

9-methyl-9-carbazole (named as compound 2 in FIG. 6)

To a solution of carbazole (5 g, 0.030 mol) in dimethylformamide (50 ml) was added portionwise sodium hydride (1.15 g, 0.030 mol) and the suspension obtained was stirred at room temperature for 0.5 hour, Iodomethane (1.43 ml, 0.030 mol) was then added dropwise. The mixture was stirred for 10 hours and ice water was then added cautiously until precipitation was complete. The precipitate was collected by filtration under vacuum, washed with water and dried in a vacuum oven. The product were thus obtained as a white solid (5.0 g, 92%). $^1$H NMR (400 MHz, $CDCl_3$): δ=8.11 (d, J=7.7 Hz, 2H), 7.48 (t, J=8.0 Hz, 2 H), 7.41 (d, J=8 Hz, 2 H), 7.24 (t, J=8 Hz, 2 H), 3.87 (s, 3 H). HRMS calcd for 181.2332, found 181.0963.

9-phenyl-9-carbazole (named as compound 3 in FIG. 6)

A mixture of iodobenzene (2.0 g, 10 mmol), carbazole (1.67 g, 10 mmol), CuI (190 mg, 1.0 mmol), L-proline (115 mg, 1.0 mmol), $K_2CO_3$ (2.8 g, 20.0 mmol), and DMSO (20 mL) was heated at 110° C. for 36 h under argon. After cooling to room temperature, the reaction was quenched with water. The mixture was extracted with $CH_2Cl_2$ and dried over $Na_2SO_4$. After the solvent had been removed, the residue was purified by column chromatography on silica gel using petroleum as eluent to give a white solid (2.23 g, 92%). $^1$HNMR (DMSO-d6, 400 Hz): δ=8.25 (d, J=7.76 Hz, 2H), 7.69 (t, J=8.0 Hz, 2H), 7.64-7.61 (m, 2H), 7.55 (t, J=7.30, 1H), 7.44 (t, J=7.4 Hz, 2H), 7.38 (d, J=8.0, 2H), 7.29 (t, J=7.32, 2H). HRMS calcd for 243.3026, found 243.1023.

Example 2

Synthesis of Compound 11, 9,9-bis(9-methylcarbazol-3-yl)-4,5-diazafluorene (named as MCAF as illustrated in FIG. 6)

Eaton's reagent (800 μL) was added under a flow of nitrogen to a solution of compound 2 (1.1 g, 6.1 mmol) and compound 1 (0.5 g, 2.8 mmol) in $CH_2Cl_2$ (5.0 mL). After the addition of Eaton's reagent, the reaction mixture was heated at 100° C. for 1 h and the escaping $CH_2Cl_2$ was collected in a cold trap. After cooled, the reaction mixture was quenched by water and neutralized with potassium carbonate. The mixture was extracted with $CH_2Cl_2$ and dried over $Na_2SO_4$ followed by evaporation of the solvent under reduced pressure. The final product was obtained through column chromatography on silica gel ($CH_2Cl_2$/Acetone=2:1) as a white solid (1.25 g, 85%). $^1$HNMR($CDCl_3$): δ=8.8 (s, 2H), 7.96 (s, 2H), 7.89 (d, J=10.4 Hz, 4H), 7.47 (t, J=8.0 Hz, 2H), 7.43-7.30 (m, 8H), 7.16 (t, J=7.28 Hz, 2H), 3.84 (s, 6H). HRMS calcd for 526.6293, found 526.1900. Anal. calcd. for $C_{37}H_{26}N_4$: C, 84.38; H, 4.98; N, 10.64. Found: C, 84.35; H, 5.01; N, 10.55.

Example 3

Synthesis of Compound 12, 9,9-bis(9-phenylcarbazaol-3-yl)-4,5-diazafluorene (named as PCAF as illustrated in FIG. 6)

Eaton's reagent (800 μL) was added under a flow of nitrogen to a solution of compound 3 (1.5 g, 6.1 mmol) and compound 1 (0.5 g, 2.8 mmol) in $CH_2Cl_2$ (5.0 mL). After the addition of Eaton's reagent, the reaction mixture was heated at 100° C. for 1 h and the escaping $CH_2Cl_2$ was collected in a cold trap. After cooled, the reaction mixture was quenched by water and neutralized with potassium carbonate. The mixture was extracted with $CH_2Cl_2$ and dried over $Na_2SO_4$ followed by evaporation of the solvent under reduced pressure. The final product was obtained through column chromatography on silica gel ($CH_2Cl_2$/Acetone=2:1) as a white solid (1.65 g, 91%). $^1$HNMR(CDCl$_3$): δ=8.79(d, 2H), 7.94(d, J=8.6 Hz, 6H), 7.76-7.52(m, 8H), 7.45(t, J=7.16 Hz, 2H), 7.38(d, J=3.6 Hz, 4H), 7.34-7.31(m, 6H), 7.21(m, 2H). HRMS calcd for 650.7681, found 650.3870. Anal. calcd. for $C_{47}H_{30}N_4$: C, 86.74; H, 4.65; N, 8.61. Found: C, 86.69; H, 4.63; N,8.63.

Example 4

With Eaton's reagent functioning as the catalyst and condensing agent, the electron-rich positions of the carbazole rings reacted efficiently with 9-positon electron-deficient carbon atom of the compound 1 to get the compounds 11 and 12. The chemical structures of the intermediates and the final products are confirmed by HNMR spectroscopy, elemental analysis, and high-resolution mass spectrometry. The molecular structure of compound 12 was further confirmed by X-ray crystallography. As shown in FIG. 7, the dihedral angle between the left carbazole and the 4,5-diazafluorene units of compound 12 (PCAF) is 65.5°, and the dihedral angle between the right carbazole and the 4,5-diazafluorene units of compound 12 is 76.0°. These twists in the molecular structure result in the reduction of the intramolecular interaction between carbazole and 4,5-diazafluorene moieties, and let compound 12 remain a high triplet energy level. Since compound 11 (MCAF) has a similar molecular structure with compound 12, the intramolecular interaction of these two compounds is the same.

Example 5

FIG. 8 and Table 1 (as shown below) demonstrate that compounds 11 and 12 exhibit nearly the same photophysical properties for their similar structures. The absorption and PL spectra of both compounds only differ in 4 nm, as illustrated in FIG. 8A. The triplet energies of compounds 11 (MCAF) and 12 (PCAF) were determined to be 2.82 eV and 2.83 eV, respectively, from the highest energy vibronic sub-band of the phosphorescence spectra at 77 K as illustrated in FIG. 8B. These values are much higher than the triplet energy of common blue phosphorescence dopants, e.g., iridium(III) bis[2-(4',6'-difluorophenyl)pyridinato-N,C(2')]-picolinate (FIrpic) (2.62 eV). Therefore, compounds 11 and 12 are appropriate host materials for organic light-emitting diode, especially for blue-emitting phosphorescent OLEDs (PHOLEDs).

Example 6

Thermal properties of compounds 11 (MCAF) and 12 (PCAF) were investigated using thermal gravimetric analysis (TGA) and differential scanning calorimetry (DSC) under a nitrogen atmosphere. Both the compounds exhibited good thermal stability (as shown in FIG. 9). Decomposition temperatures ($T_d$), which correspond to a 5% weight loss upon heating during TGA, were measured to be 395° C. and 416° C. for compounds 11 and 12, respectively. For similar non-planar molecular structures of two compounds, high glass transition temperatures ($T_g$) were distinctly observed to be 187° C. and 188° C. for compounds 11 and 12, respectively, in DCS measurements during the second heating scans. The high $T_g$ and $T_d$ values of both compounds lead to better film morphology and reduce the possibility of phase separation upon heating.

Example 7

Quantum chemical calculations were performed on compounds 11 (MCAF) and 12 (PCAF) at the B3LYP/6-31G theoretical level. As depicted in FIG. 10, the electron density distributions of the highest occupied molecular orbital (HOMO) and lowest unoccupied molecular orbital (LUMO) of these two compounds are localized predominantly on the electron-rich carbazole and electron-deficient 4,5-diazafluorene fragments, respectively, proving there are nearly no intramolecular interaction between two moieties, in consistent with our original design. The electrochemical properties of both compounds were investigated by cyclic voltammetry (CV). As shown in FIG. 11, both compounds exhibit reversible oxidation and reduction behavior, which confirm bipolar characteristics for efficient electron and hole transport. The HOMO and LUMO energy levels of compounds 11 and 12 were estimated from the half-wave potentials of the oxidation and reduction curves (relative to vacuum level), and listed in Table 1. The bandgap of compounds 11 and 12 was estimated to be 2.99 eV and 2.88 eV, respectively.

Example 8

This is an exemplary embodiment of how the compounds of the present invention are used in fabricating an organic light-emitting diode. First of all, a transparent glass and a layer of indium tin oxide (ITO) were used as a substrate and an anode, respectively. A 30-nm thick hole-transporting layer was formed by thermal evaporation of 4,4'-bis[N-(1-naphthyl)-N-phenyl amino]biphenyl (NPB). Then, 4,4',4"-tris(N-carbazolyl)triphenylamine (TCTA) with 10-nm thick was evaporated on the hole-transporting layer to form an electron-blocking layer. Subsequently, an emissive layer with a thickness of 30 nm was provided on the electron-blocking layer by

TABLE 1

Summary of physical measurements of compounds 11 and 12.

| Compound | $\lambda_{max,abs}$ [a] (nm) | $\lambda_{max,f}$ [a] (nm) | $\lambda_{max,p}$ [b] (nm) | $E_T$ (eV) | $T_g$ (° C.) | $T_m$ (° C.) | $T_d$ (° C.) | $E_{1/2}^{ox}$ (V) | HOMO (eV) | $E_{1/2}^{red}$ (V) | LUMO (eV) | $E_g$ (eV) |
|---|---|---|---|---|---|---|---|---|---|---|---|---|
| 11 | 352, 323, 301 | 380, 365 | 440 | 2.82 | 187 | 384 | 395 | 1.07 | −5.81 | −1.92 | −2.82 | 2.99 |
| 12 | 348, 320, 299 | 376, 362 | 438 | 2.83 | 188 | 362 | 416 | 0.98 | −5.72 | −1.90 | −2.84 | 2.88 |

[a] Measured in toluene solution at room temperature.
[b] Measured in 2-MeTHF glass matrix at 77 K.

co-evaporating iridium(III) bis[2-(4',6'-difluorophenyl)pyridinato-N,C(2')]-picolinate (FIrpic) as a guest molecule and compound 11 or 12 as a host material. Thereafter, 30-nm thick 1,3,5-tris(N-phenylbenzimidazol-2-yl)benzene (TPBI) was evaporated on the emissive layer. TPBI functions as a hole-blocking layer and an electron-transporting layer. Ultimately, a cathode buffer layer 9 and a cathode 10 were formed by depositing 1.5-nm thick lithium fluoride and aluminum with a thickness of 100 nm, respectively.

Example 9

Current density-luminance-voltage characteristics of the devices are shown in FIG. 12, and key device performance parameters are summarized in Table 2 as shown below. Devices using compounds 11 (MCAF) or 12 (PCAF) as a host material exhibit a low turn-on voltage of 2.6 and 2.7 V at a brightness of 1 cd/m$^2$, respectively. Considering the $E_T$ of FIrpic is about 2.62 eV, these results have already reached the limit of the FIrpic-based blue PHOLEDs. One important reason for such low turn-on voltages is the bipolar transporting property of the bipolar hosts; and another important reason is the energy level matching between the HOMO and LUMO of the two compounds. Schematic energy level diagrams of compound 11 (MCAF)-based and compound 12 (PCAF)-based OLEDs are shown in FIG. 13. It can be seen that there are nearly no injection barriers at the HTL/EML and EML/ETL junctions. Thus, both holes and electrons could easily inject into the emissive layer.

TABLE 2

The EL data of the blue PHOLEDs.

| Host | Turn-on Voltage [a] (V) | Max CE [b] (cdA$^{-1}$) | Max PE [c] (lm W$^{-1}$) | CE @ 10000 cd m$^{-2}$ (cd A$^{-1}$) | PE @ 10000 cd/m$^{-2}$ (lm W$^{-1}$) |
|---|---|---|---|---|---|
| Compound 11 | 2.6 | 32.2 | 31.3 | 27.6 | 14.5 |
| Compound 12 | 2.7 | 23.8 | 21.3 | 19.5 | 10.2 |
| mCP | 5.5 | 10.9 | 4.22 | 7.04 | 1.93 |

[a] Recorded at 1 cd m$^{-2}$.
[b] Current efficiency.
[c] Power efficiency.

FIG. 14 demonstrates that a device using compound 11 (MCAF) as a host material exhibits a maximum current efficiency of 32.2 cd/A and a very low efficiency roll-off, i.e. the efficiency maintains a high efficiency of 27.6 cd/A even at 10,000 cd/m$^2$. The power efficiency exhibits high values of 31.3 and 14.5 μm/W at 35 cd/m$^2$ and 10,000 cd/m$^2$, respectively. These values are the highest among which were ever reported for the conventional FIrpic-doped blue PHOLEDs. Compared with the MCAF-based device, the compound 12 (PCAF)-based device nearly drops its efficiency by 25%. This is because the PCAF-based device does not have singlet emission. Noting that the singlet energy levels of MCAF, PCAF, and FIrpic are 2.99, 2.88, 2.9 eV respectively, the singlet exciton transfer from PCAF to FIrpic is forbidden because of the almost the same singlet energy levels.

Example 10

For comparison, a referential device using a conventional blue host material mCP was fabricated. As shown in Table 2, the mCP-based device gives relatively poor performance with a high turn-on voltage of 5.5 V, and a low maximum efficiency of 10.9 cd/A. These huge differences between the performances of the compound 11 (MCAF)-based and mCP-based devices evidently prove the importance of the present invention.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes exemplary embodiments of the invention, these descriptions should not be viewed in a limiting sense. Rather, there are several variations and modifications which may be made without departing from the scope of the present invention as defined in the appended claims.

INDUSTRIAL APPLICABILITY

The compound of the present invention is useful as a host material for organic light-emitting diodes (OLEDs), especially blue PHOLEDs. The compound of the present invention is also useful in any devices which require highly efficient optical luminescence because of its bipolar transporting properties. The synthesis scheme of the compound is also simple and cost-effective which can lower the cost of making OLEDs.

What we claim:

1. A bipolar compound having two carbazole groups and a 4,5-diazafluorene group which is represented by formula (I),

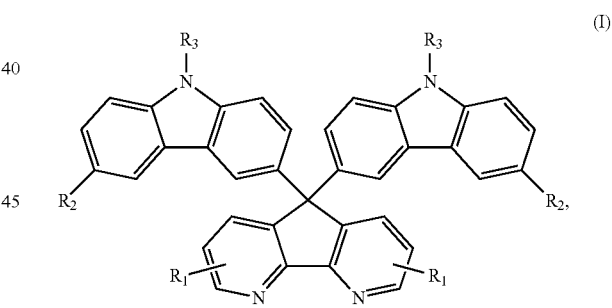

(I)

wherein R$_1$ and R$_2$ are hydrogen and R$_3$ is a methyl group or a phenyl group such that said compound exhibits a triplet energy of at least 2.82 eV, a glass transitional temperature of at least 187° C. and substantially no intramolecular interaction between said two carbazole groups and said 4,5-diazafluorene group.

2. The compound of claim 1, wherein said compound is MCAF when said R$_1$ and R$_2$ are hydrogen while said R$_3$ is methyl group such that said compound exhibits a triplet energy of at least 2.82 eV, a glass transitional temperature of at least 187° C. and substantially no intramolecular interaction between said two carbazole groups and said 4,5-diazafluorene group.

3. The compound of claim 1, wherein said compound is PCAF when said R$_1$ and R$_2$ are hydrogen while said R$_3$ is phenyl group such that said compound exhibits a triplet energy of at least 2.83 eV, a glass transitional temperature of at least 188° C. and substantially no intramolecular interaction between said two carbazole groups and said 4,5-diazafluorene group.

4. The compound of claim 1, wherein said R₁ and R₂ are hydrogen and R₃ is a methyl group or a phenyl group such that said compound exhibits a triplet energy of at least 2.82 eV, a glass transitional temperature of at least 187° C. and substantially no intramolecular interaction between said two carbazole groups and said 4,5-diazafluorene group to derive said compound into derivatives having the formula of (II) and (III):

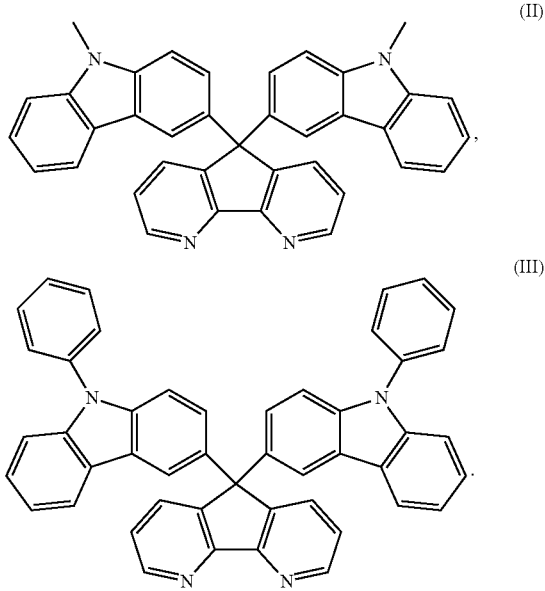

5. A device comprising an emissive layer formed by a host material made of a compound of formula (I),

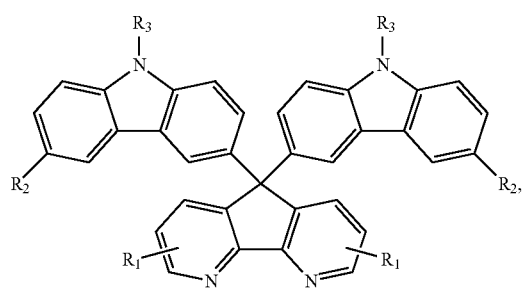

and/or the derivatives thereof, wherein R₁ and R₂ are hydrogen and R₃ is a methyl group or a phenyl group such that said compound exhibits a triplet energy of at least 2.82 eV, a glass transitional temperature of at least 187° C. and substantially no intramolecular interaction between said two carbazole groups and said 4,5-diazafluorene group, and wherein said host material is incorporated with a guest molecule to form said emissive layer which is/are sandwiched between a pair of electrode including at least one anode and one cathode.

6. The device of claim 5, additionally comprising a substrate and/or at least one of the following layers: a hole-injection layer, a hole-transporting layer, an electron-blocking layer, a hole-blocking layer, an electron-transporting layer, and/or a cathode buffer layer, wherein said at least one of said layers is/are sandwiched between said pair of electrode including at least one anode and one cathode.

7. The device of claim 6, wherein said electron-transporting layer or said hole-transporting layer comprises said compound of formula (I) such that said electron-transporting layer or said hole-transporting layer exhibits the same function of said emissive layer which is capable of emitting luminescence.

8. The device of claim 6, wherein the sequence of said layers from the bottom to the top is: the substrate, the anode, the emissive layer, and the cathode, wherein said emissive layer are substitutable by said hole-transporting layer and/or said electron-transporting layer.

9. The device of claim 6, wherein the sequence of said layers from the bottom to the top is: the substrate, the anode, the hole-transporting layer, the emissive layer, the electron-transporting layer, and the cathode, wherein the hole-injection layer is additionally sandwiched between said anode and said hole-transporting layer, and wherein the hole-blocking layer is additionally sandwiched between said emissive layer and said electron-transporting layer, and wherein the cathode buffer layer is additionally sandwiched between the electron-transporting layer and said cathode.

10. The device of claim 6, wherein said substrate is a transparent glass; said anode is indium tin oxide; said hole-transporting layer is 30 nm in thickness formed by 4,4'-bis[N-(1-naphthyl)-N-phenyl amino]biphenyl; said electron-blocking layer is 10 nm in thickness formed by 4,4',4''-tris(N-carbazolyl)triphenylamine; said emissive layer is 30 nm in thickness formed by said compound of formula (I) and/or its derivatives with said guest molecule; said hole-blocking layer or said electron-transporting layer is 30 nm in thickness formed by 1,3,5-tris(N-phenylbenzimidazol-2-yl)benzene; said cathode buffer layer is 1.5 nm in thickness formed by lithium fluoride; said cathode is 100 nm in thickness formed by aluminum, wherein said compound of formula (I) is selected from MCAF or PCAF, and wherein said guest molecule is iridium(III) bis[2-(4',6'-difluorophenyl)pyridinato-N,C(2')]-picolinate.

11. The device of claim 6, wherein said device is an organic light-emitting diode.

12. The device of claim 11, wherein said organic light-emitting diode is a blue phosphorescent organic light-emitting diode.

13. A method of making a device using an emissive layer formed by the compound of claim 1 as a host material, said method comprising:
preparing 4,5-diazafluoren-9-one;
preparing 9-methyl-9-carbazole;
preparing 9-phenyl-9-carbazole;
reacting 4,5-diazafluoren-9-one with 9-methyl-9-carbazole to form MCAF or
reacting 4,5-diazafluoren-9-one with 9-phenyl-9-carbazole to form PCAF;
co-evaporating said MCAF or said PCAF with a guest molecule to form said emissive layer;
providing a substrate as the base and a pair of electrode having an anode and a cathode; and
sandwiching said emissive layer between the pair of electrode.

14. The method of making the device of claim 13, wherein said providing of the substrate and the pair of electrode is followed by adding a hole-transporting layer on top of said anode, said hole-transporting layer is formed by thermal evaporation of 4,4'-bis[N-(1-naphthyl)-N-phenyl amino]biphenyl and fabricated into 30 nm in thickness.

15. The method of making the device of claim 14, wherein said adding of the hole-transporting layer is followed by evaporating 4,4',4"-tris(N-arbazolyl)triphenylamine with 10 nm in thickness on said hole-transporting layer to form an electron-blocking layer prior to said sandwiching of the emissive layer between the pair electrode.

16. The method of making the device of claim 15, wherein said emissive layer having 30 nm of thickness is formed by co-evaporating said MCAF or said PCAF with iridium(III) bis[2-(4',6'-difluorophenyl)pyridinato-N,C(2')]-picolinate as said guest molecule on said hole-transporting layer prior to said sandwiching.

17. The method of making the device of claim 16, wherein said co-evaporating is followed by evaporating 1,3,5-tris(N-phenylbenzimidazol-2-yl)benzene on said emissive layer to form the hole-blocking layer or the electron transporting layer in 30 nm of thickness.

18. The method of making the device of claim 17, wherein the cathode buffer layer is formed by depositing lithium fluoride in 1.5 nm of thickness prior to said sandwiching.

19. The method of making the device of claim 13, wherein said cathode is formed by aluminum in 100 nm of thickness.

20. The method of making the device of claim 13, wherein said device is an organic light-emitting diode.

21. The method of making the device of claim 20, wherein said organic light-emitting diode is a blue phosphorescent organic light-emitting diode.

* * * * *